United States Patent [19]

Adrian et al.

[11] Patent Number: 4,596,254
[45] Date of Patent: Jun. 24, 1986

[54] LASER DOPPLER FLOW MONITOR

[75] Inventors: Ronald J. Adrian, Champaign, Ill.; John A. Borgos, St. Paul, Minn.

[73] Assignee: TSI Research Associates Limited Partnership, Minneapolis, Minn.

[21] Appl. No.: 682,986

[22] Filed: Dec. 18, 1984

[51] Int. Cl.$^4$ ................................................. A61B 5/02
[52] U.S. Cl. ..................................... 128/666; 128/691; 356/28
[58] Field of Search .................... 128/666, 663, 691; 356/28

[56] References Cited

U.S. PATENT DOCUMENTS

| | | |
|---|---|---|
| 3,313,290 | 4/1967 | Chance et al. |
| 3,511,227 | 5/1970 | Johnson . |
| 3,532,427 | 10/1970 | Paine . |
| 3,552,855 | 1/1971 | Crosswy et al. |
| 3,584,956 | 6/1971 | Hines ................................... 356/28 |
| 3,647,299 | 3/1972 | Lavallee . |
| 3,709,599 | 1/1973 | Iten . |
| 3,795,447 | 3/1974 | Welch et al. |
| 3,814,081 | 6/1974 | Mori . |
| 3,830,222 | 8/1974 | Chance . |
| 4,109,647 | 8/1978 | Stern et al. |
| 4,476,875 | 10/1984 | Nilsson et al. ........................ 128/666 |

OTHER PUBLICATIONS

Duteil et al., IEEE Trans. Biomed. Engr., vol. BME-32, No. 6, Jun. 1985, pp. 439-447.
Yogamathan et al., Med. & Biol. Eng. & Comput, vol. 17, No. 1, Jan. 1979, pp. 38-44.
Tanaka et al., Applied Optics, vol. 14, No. 1, Jan. 1975, pp. 189-196.

Wunderlich et al., Rev. Sci. Instrum., vol. 51(9), Sep. 1980, pp. 1258-1262.
"In Vivo Evaluation of Microcirculation by Coherent Light Scattering" Nature, vol. 254, Mar. 6, 1975, pp. 56-58.
"High Speed Correlation Techniques," SI Quarterly, vol. VIII, issue 2, Apr.-Jun. 1982, pp. 3-12.
"Model for Laser Doppler Measurements of Blood Flow in Tissue" Applied Optics, vol. 20, No. 12, Jun. 15, 1981, pp. 2097-2107.

Primary Examiner—Kyle L. Howell
Assistant Examiner—John C. Hanley
Attorney, Agent, or Firm—Burd, Bartz & Gutenkauf

[57] ABSTRACT

A method and apparatus for measuring the velocity of moving particles such as red blood cells in a tissue sample is disclosed, characterized by digital processing techniques and autocorrelation. The moving particles are illuminated to produce a spread spectrum optical signal resulting from the Doppler shift occurring when photons are scattered by the moving particles. A spread spectrum electrical signal corresponding with the optical signal and containing spectral and noise components is generated from the optical signal. The electrical signal is filtered to produce the bandpass and DC signals which are subsequently converted to digital form. A first autocorrelation function is calculated from the bandpass signal and a noise autocorrelation function is determined in accordance with the DC signal level. The first and noise autocorrelation functions are compared to produce an autocorrelation function free of a noise component. From the autocorrelation function, the mean frequency of the electrical signal is linearly calculated, the mean frequency corresponding with the average velocity of the moving particles.

8 Claims, 1 Drawing Figure

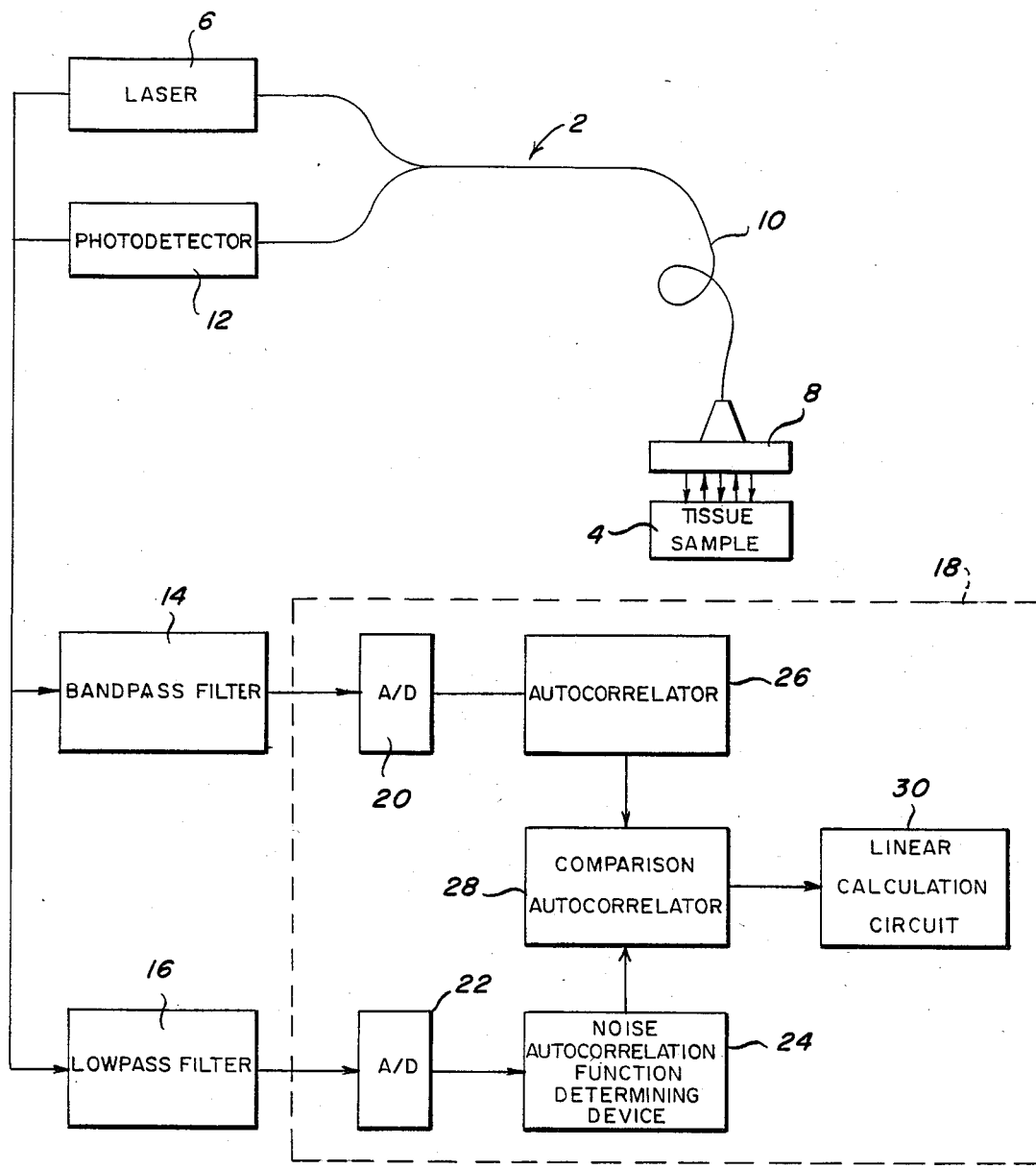

LASER DOPPLER FLOW MONITOR

BACKGROUND OF THE INVENTION

The present invention relates to a method and apparatus for measuring the average velocity of red blood cells in a microvascular bed through digital processing of an electrical signal corresponding with a spread spectrum optical signal generated by the Doppler shift resulting when the red blood cells are illuminated.

BRIEF DESCRIPTION OF THE PRIOR ART

Laser Doppler flow measuring methods and devices are well-known in the patented prior art as evidenced by the patents to Johnson U.S. Pat. No. 3,511,227, Paine U.S. Pat. No. 3,532,427, Crosswy et al U.S. Pat. No. 3,552,855, Hines et al U.S. Pat. No. 3,584,956, Iten U.S. Pat. No. 3,709,599, Welch et al U.S. Pat. No. 3,795,447, and Stern et al U.S. Pat. No. 4,109,647. The Johnson patent, for example, discloses a method for measuring blood flow characteristics using coherent radiation and the Doppler effect. The frequency of the radiation scattered by particles in the blood is compared with the frequency of the original radiation to determine the flow characteristics of the blood. While the method of the Johnson patent is suitable for measuring blood flow rates in a relatively large vessel, it did not prove to be accurate for measuring blood flow in a tissue sample.

Accordingly, the method and apparatus for measuring blood flow as disclosed in the Stern et al patent was developed. More particularly, light from an illuminated tissue is delivered to a photodiode which produces output spectrum signals which are differentiated and subsequently delivered to a root-mean-square detector. The output from the detector is fed to a calculating circuit to formulate a blood flow parameter.

While the method and apparatus of the Stern et al patent normally perform quite satisfactorily, they suffer the inherent drawbacks with regard to accuracy of calculation of flow velocity resulting from the use of unreliable parameters in the calculation. The present invention was developed in order to overcome these and other drawbacks of the prior art by providing a method and apparatus for measuring the average velocity of red blood cells in a tissue sample using digital processing of an autocorrelation function corresponding to the optical signal generated by exposing the tissue sample to illumination.

SUMMARY OF THE INVENTION

Accordingly, it is a primary object of the present invention to provide a method and apparatus for measuring the speed of moving particles such as red blood cells in a tissue sample. The particles are preferably illuminated by a laser beam directed at the sample via a fiber optic bundle. Illumination of the particles produces a spread spectrum optical signal owing to the Doppler shift occurring when photons are scattered by the moving particles. The optical signal is converted to a spread spectrum electrical signal having spectral and noise components. Noise is filtered from the electrical signal to produce a bandpass signal and AC components are filtered from the electrical signal to produce a DC signal proportional to the optical signal. The bandpass and DC signals are converted to digital form and processed to calculate the mean frequency of the electrical signal, with the mean frequency corresponding with the average speed of the moving particles. More particularly, a first autocorrelation function is calculated from the bandpass signal. The DC signal level is sensed and a noise autocorrelation function corresponding thereto is determined. The first and noise autocorrelation functions are compared to produce an autocorrelation function free of a noise component. From the autocorrelation function, the mean frequency is linearly calculated.

According to a more specific object of the invention, the first autocorrelation function is a single-clipped autocorrelation function.

According to a further object of the invention, digital processing techniques are employed, thereby avoiding the requirement for tuning of the circuits as is necessary with analog processing schemes.

It is another object of the invention to remove the undesirable noise component from the electrical signal by computing the noise level in real time and continuously correcting for it.

BRIEF DESCRIPTION OF THE FIGURES

Other objects and advantages of the subject invention will become apparent from a study of the following specification when viewed in the light of the accompanying sole FIGURE of drawing which is a block diagram illustrating the apparatus for measuring the velocity of moving particles in a sample according to the invention.

DETAILED DESCRIPTION

As shown in the drawing, an optical system 2 is provided for illuminating a tissue sample 4 containing a plurality of red blood cells whose velocity is to be measured. The optical system includes a laser source 6 connected with an optical transducer 8 via a bidirectional fiber optic bundle 10. The optical transducer 8 is arranged adjacent the sample and transmits laser energy to the tissue and receive an optical signal therefrom. More particularly, when the tissue sample is illuminated with coherent light, some of the light penetrates the tissue, is randomly scattered by both stationary tissue elements and moving red blood cells, and emerges from the tissue sample. A portion of this light is received by the transducer and delivered as an optical signal to a photodetector 12 such as a photodiode by the fiber optic bundle 10.

The optical signal received by the photodetector has a broadened spectrum resulting from the Doppler shifting that occurs when photons are scattered by moving particles. The photodetector converts the optical signal into an electrical signal having the same spectral shape centered around zero frequency. The width of this spectrum is proportional to the average speed of the moving red blood cells. See Bonner, R. and Nossal, R., "Model for Laser Doppler Measurements of Blood Flow in Tissue", Applied Optics, Vol. 20, No. 12, June 15, 1981, pages 2097–2107.

The electrical signal produced by the photodetector includes both spectral components resulting from the Doppler effect as set forth above and undesirable noise components. The noise represents shot noise and amplifier noise, both of which are uncorrelated with the spectral components. Accordingly, a bandpass filter 14 is connected with an output of the photodetector. The bandpass filter removes unwanted noise from the electrical signal at both high and low frequencies. For measuring blood perfusion in tissue, the bandpass is preferably between 30 and 20,000 Hz.

A low-pass filter 16 is also connected with an output of the photodetector. The low-pass filter removes from the electrical signal all but the DC component which is proportional to the total light intensity received by the photodetector.

The bandpass signal from the bandpass filter 14 and the DC signal from the low-pass filter 16 are delivered to a signal processor 18 which calculates the mean frequency of the electrical signal, the mean frequency corresponding with the average velocity of the red blood cells of the tissue sample.

The signal processor 18 includes a first analog-to-digital converter 20 connected with the output of the bandpass filter 14 to convert the bandpass signal to digital form. Similarly, a second analog-to-digital converter 22 connected with the output of the low-pass filter 16 converts the DC signal to digital form.

The digital DC signal is delivered to a noise autocorrelation function computation device 24 which determines the noise power and a noise autocorrelation function, both of which depend on the total light intensity received by the photodetector. In essence, the device 24 contains information on the relationship between the noise autocorrelation function and the DC signal level, the relationship being previously defined such as by measuring the noise autocorrelation function for each of several DC levels. The digital bandpass signal is delivered to an autocorrelation circuit 26 for calculation of a single-clipped autocorrelation function of the bandpass signal which has both signal and noise information. The outputs of the noise autocorrelation function computation device 24 and of the autocorrelation circuit 26 are delivered to a comparison autocorrelation circuit 28 where the noise contribution to the signal is removed, thereby to provide an autocorrelation function output which is delivered to a linear calculation circuit 30 for calculation of the mean absolute frequency of the blood flow optical signal.

MEAN FREQUENCY COMPUTATION

A characteristic of many electrical signals including that produced by the photodetector 12 and corresponding with the optical signal from the tissue sample is that a spectrum of frequencies is present. It is useful to define a power spectrum, $P(\omega)$, of the electrical signal, $e(t)$, as follows:

$$P(\omega) = \left| \int_{-\infty}^{\infty} e(t) \cdot e^{-j\omega t} dt \right|^2. \quad (1)$$

In practice, this integration may be performed over many finite time intervals, and the resultant functions $P(\omega)$ may be added together.

It is also useful to compute certain moments of the power spectrum. The $n^{th}$ moment (for a spectra symmetric about zero frequency) is defined as:

$$<\omega^n> = \int_O^\infty \omega^n P(\omega) d\omega \Big/ \int_O^\infty P(\omega) d\omega. \quad (2)$$

As can be readily seen, the measurement of any moment of the power spectrum requires first the computation of a large number of power spectra (usually 1000 or more) and the subsequent computation of the $n^{th}$ moment from the average power spectrum. For many laboratory instruments, the cost of hardware to do all this is prohibitive.

The present invention makes use of the fact that the autocorrelation function (ACF) of the electrical signal contains the necessary spectral information, thus eliminating the need to perform the Fourier transformations as defined in Equation 1. The ACF of a real-time electrical signal is defined as $R_{SS}(\tau)$, where $$R_{SS}(\tau) = <e_S(t) \cdot e_S(t+\tau)>. \quad (3)$$

For signals with a broad spectrum of frequencies, such as the photodetector output containing blood perfusion information, this function will typically be somewhat normal (i.e., Gaussian) in shape, and its characteristic width will, in general, vary inversely with the first moment of the power spectrum.

The relationship between the ACF and the power spectrum is defined by the Fourier transform of the ACF:

$$P(\omega) = \frac{1}{2\pi} \int_{-\infty}^{\infty} e^{-j\omega\tau} R_{SS}(\tau) d\tau. \quad (4)$$

Making use of Equations 4 and 2, one obtains:

$$<\omega> = \frac{\int_O^\infty \omega d\omega \cdot \frac{1}{2\pi} \left[ \int_{-\infty}^\infty e^{-j\omega\tau} R_{SS}(\tau) d\tau \right]}{\int_O^\infty P(\omega) d\omega} \quad (5)$$

$$= \frac{\frac{1}{2\pi} \int_{-\infty}^\infty R_{SS}(\tau) d\tau \cdot \left[ \int_O^{\omega_m} \omega e^{-j\omega\tau} d\omega \right]}{\int_O^\infty P(\omega) d\omega} \quad (6)$$

$$= \frac{2}{\pi \cdot R_{SS}(O)} \int_O^\infty R_{SS}(\tau) \cdot \quad (7)$$

$$\left[ \frac{\cos(\omega_m \tau) + \omega_m \tau \sin\omega_m \tau - 1}{\tau^2} \right] d\tau$$

where $\omega_m$ may be arbitrarily chosen, but is a frequency beyond which the power spectrum is negligible, possibly by virtue of having filtered $e(t)$ to eliminate any frequencies greater than $\omega_m$. Since the ACF generally is measured only at discrete values of $\tau$ (i.e., the measurement is not continuous), it is convenient to replace the integral with a summation over the ACF. Hence, if $$I(\tau) = \frac{\cos(\omega_m \tau) + \omega_m \tau \sin(\omega_m \tau) - 1}{\tau^2}, \quad (8)$$

then $$<\omega> = \frac{2}{\pi \cdot R_{SS}(O)} \cdot \sum_{i=0}^{N} R_{SS}(i\Delta\tau) \cdot I(i\Delta\tau) \cdot \Delta\tau, \quad (9)$$

where $\Delta\tau$ is the interval between discrete time values in the ACF, and $\tau_{max} = N\Delta\tau$ is the maximum time delay.

The relationship set forth in Equation 9 allows the direct computation of a mean frequency (i.e. the first moment) by a linear operation on the autocorrelation function of the real-time electrical signal. It should be appreciated that the actual implementation of this concept requires the selection of a value $\omega_m$, and that this selection will in part be controlled by the value of $\Delta\tau$. It should also be appreciated that the discrete values of the function $I(\tau)$ might be assigned so as to give a certain weighting to certain regions of the power spectrum, or to optimize the noise rejection, or to obtain some other purpose. In addition, while Equations 5-7 show how the first moment of the power spectrum might be obtained, obviously in principle it is possible to obtain the higher moments in an analogous fashion. Moreover, because the execution of Equation 9 might typically be done with a microcomputer, it is possible to substitute different functions $I(\tau)$ by means of software modifications, making this device extremely flexible.

SINGLE CLIPPING

The measurement of the function $R_{SS}(\tau)$ (Equation 3) involves the use of a signal correlator. In order to obtain a statistically valid estimate of $R_{SS}(\tau)$, the correlator must obtain many samples of the product $e(t)\,e(t+\tau)$ for each value of the time delay $\tau$.

An alternative method that is utilized by the present invention is to obtain a single-clipped ACF of the electrical signal; i.e., $$R_{S_1 S}(\tau) = \langle e_{1,s}(t) \cdot e_s(t+\tau) \rangle. \tag{10}$$

where $e_1(t)$ is the one-bit quantization of the electrical signal (i.e., either $+1$ or $-1$, corresponding to the sign of $e(t)$). For many types of electrical signals, including the photodetector output containing blood flow information, this does not cause a distortion in the shape of the ACF. See, Adrian, Ronald J., "High Speed Correlation Techniques" TSI Quarterly, Vol. VIII, Issue 2, April–June 1982, pages 3-12. The advantage of this clipping technique is that no actual multiplication of the signals is required; the multiply operation is replaced by a simple assignment of an arithmetic sign ($+$ or $-$).

NOISE CORRELATION

The electrical signal from the photodetector 12 which contains blood flow information, also contains undesirable noise. This noise arises largely from the amplifier of the photodetector current signal and from shot noise in the photodetector. This noise can be ignored when the light intensity is high enough, but must be considered when the light intensity is reduced to levels that are acceptable in a routinely used clinical instrument.

The single-clipped ACF of the noise is defined in the same way as the single-clipped ACF of the blood flow signal (see Equation 10);

$$R_{n_1 n}(\tau) = \langle c_{1,n}(t) \cdot e_n(t+\tau) \rangle. \tag{11}$$

It is covenient to define the blood flow signal plus noise as:

$$u = S + n \tag{12}$$

The single-clipped correlation of the blood flow signal plus noise is also defined as in Equation 10:

$$R_{u_1 u}(\tau) = \langle e_{1,u}(t) \cdot e_u(t+\tau) \rangle. \tag{13}$$

where $e_u$ is the electrical signal corresponding to the blood flow signal plus the noise.

In practice, it is a part of the operation of this apparatus to measure the function $R_{u_1 u}(\tau)$. The present invention relates to the method for correcting this ACF to remove the effect of unwanted noise, in order to obtain the ACF of the blood flow signal alone, namely $^R S_1 S(\tau)$. Further, the method determines $R_{SS}(\tau)/R_{SS}(0)$, which is used directly to determine the mean frequency (see equation 9).

Essentially, the noise correction is performed as follows:

$$\frac{R_{SS}(\tau)}{R_{SS}(O)} = \frac{R_{u_1 u}(O) R_{u_1 u}(\tau) - R_{n_1 n}(O) R_{n_1 n}(\tau)}{R_{u_1 u}^2(O) - R_{n_1 n}^2(O)}. \tag{14}$$

A typical operating procedure for the instrument would be as follows:
1. A measurement is made of the single-clipped noise ACF in the photodetector electrical output, as defined in Equation 11.
2. The ACF of the photodetector output, containing both noise and blood flow information, is measured, as defined in Equation 13.
3. The corrected ACF of the blood flow signal alone is computed, as per Equation 14.
4. The desired moment (e.g., $\langle\omega\rangle$) of the power spectrum is computed, using a previously selected set of values for $I(\tau)$, as per Equation 9, for example.

It should be appreciated that numerous simplifications can be made to minimize the computation effort without significantly altering the concepts involved. For example, the noise power can be assumed to be constant, or can be assumed to be a repeatable function of the total light intensity on the photodetector. Also, the noise correction to the desired moment can be made by measuring the moment due to the noise alone, and due to blood flow signal plus noise, and correcting the blood flow signal plus noise moment using the equations implied by Equations 9 and 14.

While in accordance with the provisions of the Patent Statutes the preferred forms and embodiments of the invention have been illustrated and described, it will be apparent to those skilled in the art that various changes and modifications may be made without deviating from the inventive concepts set forth above.

What is claimed is:
1. Apparatus for measuring the velocity of particles moving in a media comprising:
   (a) means for illuminating the particles to produce a spread spectrum optical signal resulting from the Doppler shift occurring when photons are scattered by the moving particles;
   (b) photodetector means connected with said optical illumination means for producing a spread spectrum electrical signal corresponding with said optical signal, said electrical signal containing spectral and noise components;
   (c) first filter means connected with said photodetector means for filtering noise from said electrical signal at high and low frequencies;
   (d) second filter means connected with said photodetector means for producing a DC signal proportional to the total optical signal received by said photodetector means; and

(e) signal processing means connected with said first and second filter means for calculating the mean frequency of said spread spectrum electrical signal, the mean frequency corresponding with the average velocity of the moving particles, said processing means including
  (1) first and second analog-to-digital converter means connected with said first and second filter means, respectively, for converting said electrical signal from the first filter means and said DC signal to digital signals;
  (2) first correlation means connected with said first converter means for calculating a first autocorrelation function from said digital signal from the first filter means;
  (3) means connected with said second converter means for determining a noise autocorrelation function from said digital DC signal;
  (4) means connected with said first correlation means and said noise autocorrelation function determining means for comparing said noise autocorrelation function with said first autocorrelation function and for producing an autocorrelation function free of a noise component; and
  (5) linear calculation means connected with said autocorrelation comparison means for calculating the mean frequency from the autocorrelation function.

2. Apparatus as defined in claim 1, wherein said illuminating means comprises a laser source connected to an optical fiber.

3. Apparatus as defined in claim 2, wherein said first correlation means comprises means for calculating a single-clipped autocorrelation function.

4. Apparatus for measuring the velocity of moving blood cells in a tissue sample, comprising
  (a) means for illuminating the blood cells to produce a spread spectrum optical signal resulting from the Doppler shift occurring when photons are scattered by the moving blood cells;
  (b) photodetector means connected with said optical illumination means for producing a spread spectrum electrical signal corresponding with said optical signal, said electrical signal containing spectral and noise components;
  (c) bandpass filter means connected with said photodetector means for filtering noise from said electrical signal at high and low frequencies;
  (d) low-pass filter means connected with said photodetector means for producing a DC signal proportional to the total optical signal received by said photodetector means; and
  (e) signal processing means connected with said bandpass and low-pass filter means for calculating the mean frequency of said spread spectrum electrical signal, the mean frequency corresponding with the average velocity of the moving blood cells, said processing means including
  (1) first and second analog-to-digital converter means connected with said bandpass and low-pass filter means, respectively, for converting said bandpass signal and said DC signal to digital signals;
  (2) first correlation means connected with said first converter means for calculating a first autocorrelation function from said digital bandpass signal;
  (3) means connected with said second converter means for determining a noise autocorrelation function from said digital DC signal;
  (4) means connected with said first correlation means and said noise autocorrelation function determining means for comparing said noise autocorrelation function with said first autocorrelation function to produce an autocorrelation function free of a noise component; and
  (5) liner calculation means connected with said autocorrelation comparison means for calculating the mean frequency from the autocorrelation function.

5. Apparatus as defined in claim 1, wherein said illuminating means comprises a laser source connected to an optical fiber.

6. Apparatus as defined in claim 2, wherein said first correlation means comprises means for calculating a single-clipped autocorrelation function.

7. A method for measuring the velocity of particles moving in a media, comprising the steps of
  (a) illuminating the particles to produce a spread spectrum optical signal resulting from the Doppler shift occurring when photons are scattered by the moving particles;
  (b) generating a spread spectrum electrical signal corresponding with said optical signal and containing spectral and noise components;
  (c) filtering noise from said electrical signal at high and low frequencies to produce a bandpass signal and filtering AC components from said electrical signal to produce a DC signal proportional to said optical signal;
  (d) converting said bandpass and DC signals to digital signals;
  (e) calculating a first autocorrelation function from said digital bandpass signal and a noise autocorrelation function from said digital DC signal;
  (f) comparing said first and noise autocorrelation functions to produce an autocorrelation function free of a noise component; and
  (g) calculating the mean frequency from the autocorrelation function, the mean frequency corresponding with the average velocity of the moving particles.

8. A method for measuring the velocity of moving blood cells in a tissue sample, comprising the steps of
  (a) illuminating the blood cells to produce a spread spectrum optical signal resulting from the Doppler shift occurring when photons are scattered by the moving blood cells;
  (b) generating a spread spectrum electrical signal corresponding with said optical signal and containing spectral and noise components;
  (c) filtering noise from said electrical signal at high and low frequencies to produce a bandpass signal;
  (d) filtering AC components from said electrical signal to produce a DC signal proportional to said optical signal;
  (e) converting said bandpass signal and said DC signal to digital signals;
  (f) calculating a first autocorrelation function from said digital bandpass signal;
  (g) calculating a noise autocorrelation function from said digital DC signal;
  (h) comparing said first and noise autocorrelation functions to produce an autocorrelation function free of a noise component; and
  (i) calculating the mean frequency from the autocorrelation function, the mean frequency corresponding with the average velocity of the moving blood cells.

* * * * *